(12) United States Patent
Katou et al.

(10) Patent No.: US 8,822,920 B2
(45) Date of Patent: Sep. 2, 2014

(54) CHARGED PARTICLE BEAM APPARATUS

(75) Inventors: Tatsuichi Katou, Hitachinaka (JP); Satoshi Takada, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 13/808,608

(22) PCT Filed: Jun. 15, 2011

(86) PCT No.: PCT/JP2011/003392
§ 371 (c)(1),
(2), (4) Date: Jan. 7, 2013

(87) PCT Pub. No.: WO2012/008091
PCT Pub. Date: Jan. 19, 2012

(65) Prior Publication Data
US 2013/0105690 A1 May 2, 2013

(30) Foreign Application Priority Data

Jul. 15, 2010 (JP) ................................. 2010-160196

(51) Int. Cl.
*H01J 37/26* (2006.01)
(52) U.S. Cl.
USPC ........... 250/307; 250/306; 250/310; 250/311; 250/396 R; 250/397
(58) Field of Classification Search
USPC ............. 250/306, 307, 309, 310, 311, 396 R, 250/397, 398
See application file for complete search history.

(56) References Cited

U.S. PATENT DOCUMENTS

| | | | |
|---|---|---|---|
| 5,412,209 A | 5/1995 | Otaka et al. | |
| 2006/0060781 A1* | 3/2006 | Watanabe et al. | ............. 250/310 |
| 2006/0289755 A1 | 12/2006 | Koyama et al. | |
| 2009/0050802 A1 | 2/2009 | Noji et al. | |

FOREIGN PATENT DOCUMENTS

| | | |
|---|---|---|
| EP | 0 810 629 A1 | 12/1997 |
| JP | 5-151927 | 6/1993 |
| JP | 2006-338881 | 12/2006 |
| JP | 2009-180627 | 8/2009 |
| WO | WO 2007/086400 A1 | 8/2007 |

* cited by examiner

*Primary Examiner* — Nicole Ippolito
(74) *Attorney, Agent, or Firm* — Antonelli, Terry, Stout & Kraus, LLP.

(57) ABSTRACT

In recent years, in association with the miniaturization and high integration of semiconductor manufacturing processes, there have been arising many cases where observation target portions are densely located. In such a case, if observation is performed using a conventional pre-charge technology, scanning with an electron beam in pre-charging are repeatedly executed, therefore the charge potential on the surface of a specimen exceeds the dielectric breakdown voltage. As a result, dielectric breakdown arises in areas where scanning with an electron beam are repeatedly executed. An object of the present invention is to provide a defect observation method that can reduce the risk of dielectric breakdown, and a charged particle beam apparatus that utilizes the method. In the present invention, when a specimen is observed with the use of a technology relevant to pre-charging, after executing a piece of control processing, plural images are photographed. In addition, by grouping observation target portions, which plural pre-charge scanning areas overlap, into a group where charge control is executed all together on all the observation target portions, and by executing charge control processing on each group, the risk of dielectric breakdown is reduced.

14 Claims, 13 Drawing Sheets

(a) IN THE CASE WHERE PRE-CHARGING IS NOT USED

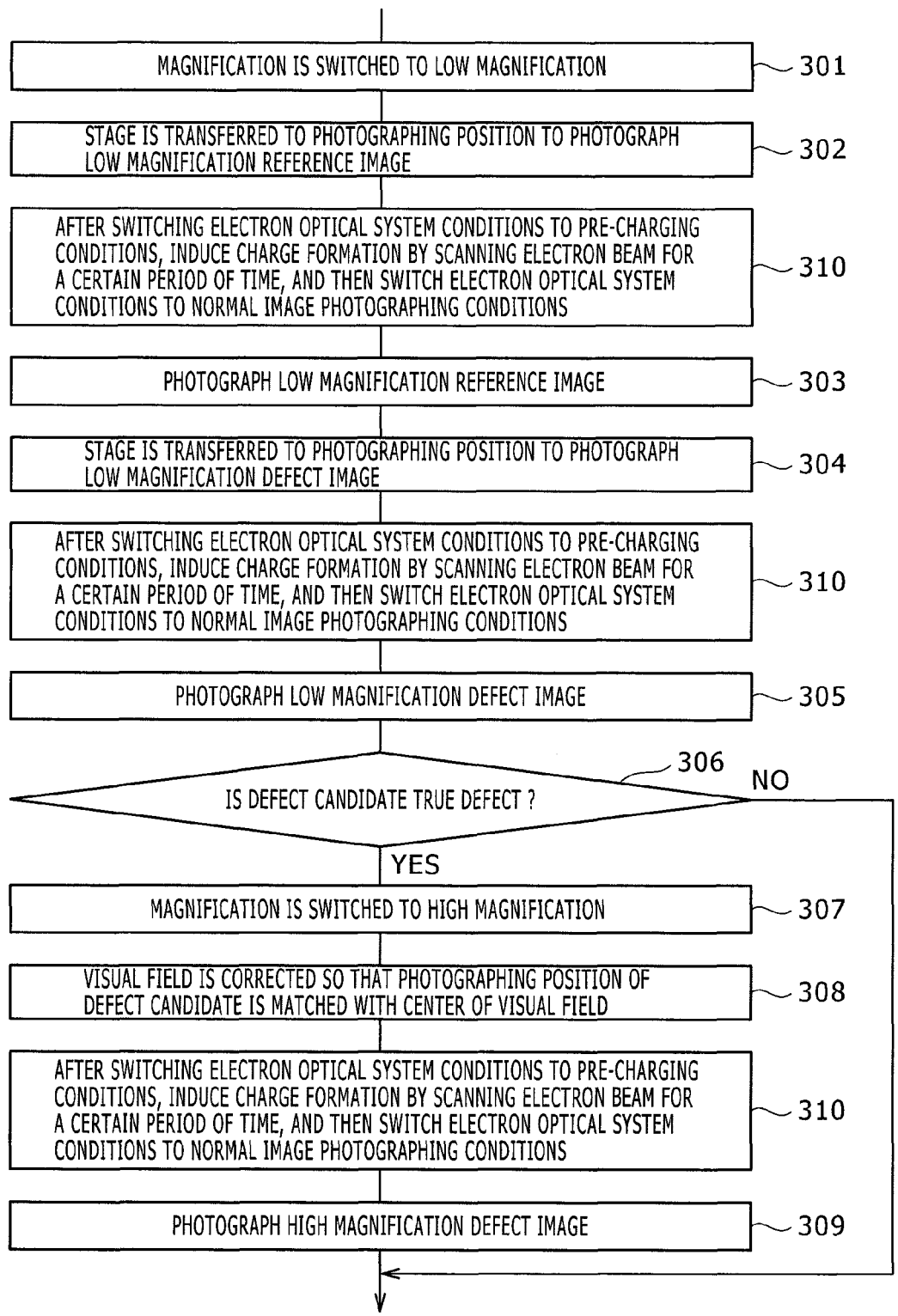
(b) IN THE CASE WHERE PRE-CHARGING IS USED

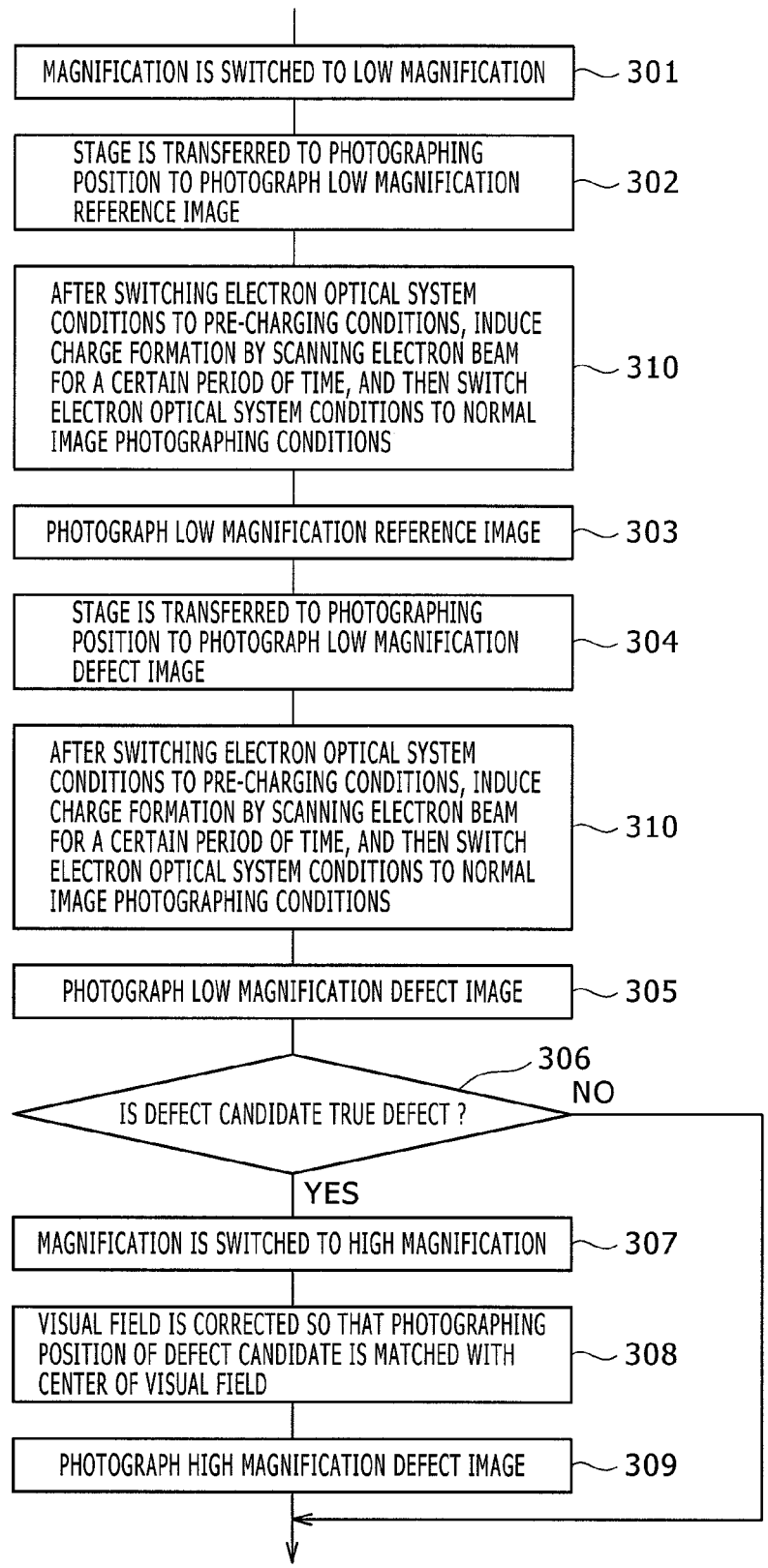

CHARGED PARTICLE BEAM APPARATUS

TECHNICAL FIELD

The present invention relates to a charged particle beam apparatus and a scanning electron microscope for photographing the image of an observation target portion on a specimen, and more particularly relates to a technology of charging the specimen before photographing the image of the observation target portion.

BACKGROUND ART

As a means for observing portions that appear to be defects (hereinafter referred to as defect candidates) and are located at unspecified coordinate positions on a specimen (for example, on a semiconductor wafer) with the use of a charged particle beam, a charged particle beam apparatus (Defect Review SEM: DR-SEM) that automatically detects defects, observes the shapes of the defects, etc., and classifies the defects on the basis of an inspection result that is obtained in advance using an optical or electron beam defect inspection apparatus has been used. Defects are observed as follows with the use of the DR-SEM. First, a reference image that is used for being compared with a defect candidate and an image of the defect candidate are photographed at a low magnification. Both images will be referred to as a low magnification reference image and a low magnification defect image respectively hereinafter. With the use of the difference between both images, an accurate coordinate position of the defect candidate is specified. Subsequently, in order to easily judge whether the defect candidate is a true defect or not, the defect image is photographed at a high magnification (the defect image photographed at a high magnification will be referred to as a high magnification defect image hereinafter), and after a process that automatically detects a defect (Automatic Defect Review: ADR) is executed on the high magnification defect image, whether the defect candidate is a true defect or not is judged. In addition, with the use of a process that automatically classifies a defect (automatic defect classification: ADC), various classifications of shapes and the like are executed on the basis of the defect image.

In recent years, in association with the miniaturization and high integration of semiconductor manufacturing processes, the thicknesses of insulating films have been getting larger. Therefore, the depths of contact holes have been getting larger, the diameters of contact holes have been getting smaller, and the grooves of wiring patterns have been made deeper, with the result that the detection of defects relevant to a high aspect ratio (for example, a ratio between the depth and diameter of a contact hole) has been widely performed. However, ordinary electron beam scanning cannot uniformly charge a contact hole to its bottom, hence a potential contrast clear enough to detect a defect as a secondary electron image cannot be obtained. Therefore, it is necessary to irradiate an electron beam to form charge before photographing an image (irradiating an electron beam in advance will be referred to pre-charging hereinafter) to at least an area to be photographed on the surface of a specimen, that is, charge formation processing has to be executed in advance. For example, disclosed in Patent Literature 1 is a technology in which pre-charging is executed by scanning an electron beam to an area broader than an area to be photographed by switching from the magnification of photographing to a lower magnification. Hereinafter the area scanned with an electron beam in pre-charging will be referred to as a pre-charge scanning area.

The charge formation processing is used not only for defect detection but also for a charged particle beam apparatus (for example, Critical Dimension SEM: CD-SEM) in which the measurement of the shape, dimensions, etc. of a micropattern formed on a specimen are performed.

In the above mentioned charged particle beam apparatuses, because time required for the stage transfer occupies a large portion of time for inspecting one observation target, Patent Literature 2 proposes a technology in which time required for the stage transfer and the number of pieces of photographing can be reduced by grouping defect candidates within a certain distance so that these defect candidates are brought into one visual field and by inspecting these defect candidates afterward.

CITATION LIST

Patent Literature

Patent Literature 1: Japanese Unexamined Patent Application Publication No. Hei5 (1993)-151927 (The corresponding United States Patent is U.S. Pat. No. 5,412,209)
Patent Literature 2: Japanese Unexamined Patent Application Publication No. 2009-180627

SUMMARY OF INVENTION

Technical Problem

As described above, in order to detect a defect, it is necessary to raise a potential contrast by executing charge control processing on a specimen, while there is a possibility that dielectric breakdown occurs because of repeated irradiation of an electron beam used in the above mentioned charge processing if the specimen is made of semiconductor and the like.

Therefore, it is an object of the present invention to provide a defect observation method that can reduce the risk of dielectric breakdown, and a charged particle beam apparatus that utilizes the method.

Solution to Problem

After defect candidates on which charge control processing is executed all together are automatically or manually determined, plural images regarding the defect candidates are photographed in a piece of charge control processing.

In addition, the determination of defect candidates on which charge control processing is executed all together is made by grouping candidates included in a common pre-charge scanning area. The central position of the pre-charge scanning area for each group is set by adjustment. Pre-charging for defect candidates grouped in each group before photographing defect images of the defect candidates is executed all together, and afterward the images of the defect candidates located in the corresponding pre-charge scanning area are photographed.

Advantageous Effects of Invention

According to the present invention, the risk of dielectric breakdown can be reduced and specimens can be safely observed.

BRIEF DESCRIPTION OF DRAWINGS

FIG. 3(b) is a flow chart of an ordinary detection sequence in the case where pre-charging is executed.

FIG. 14 is a flowchart in the case where a low magnification defect image and a high magnification defect image are photographed after common pre-charging is executed.

DESCRIPTION OF EMBODIMENTS

Embodiments will be described with reference to the accompanying drawings.

Figure 1:
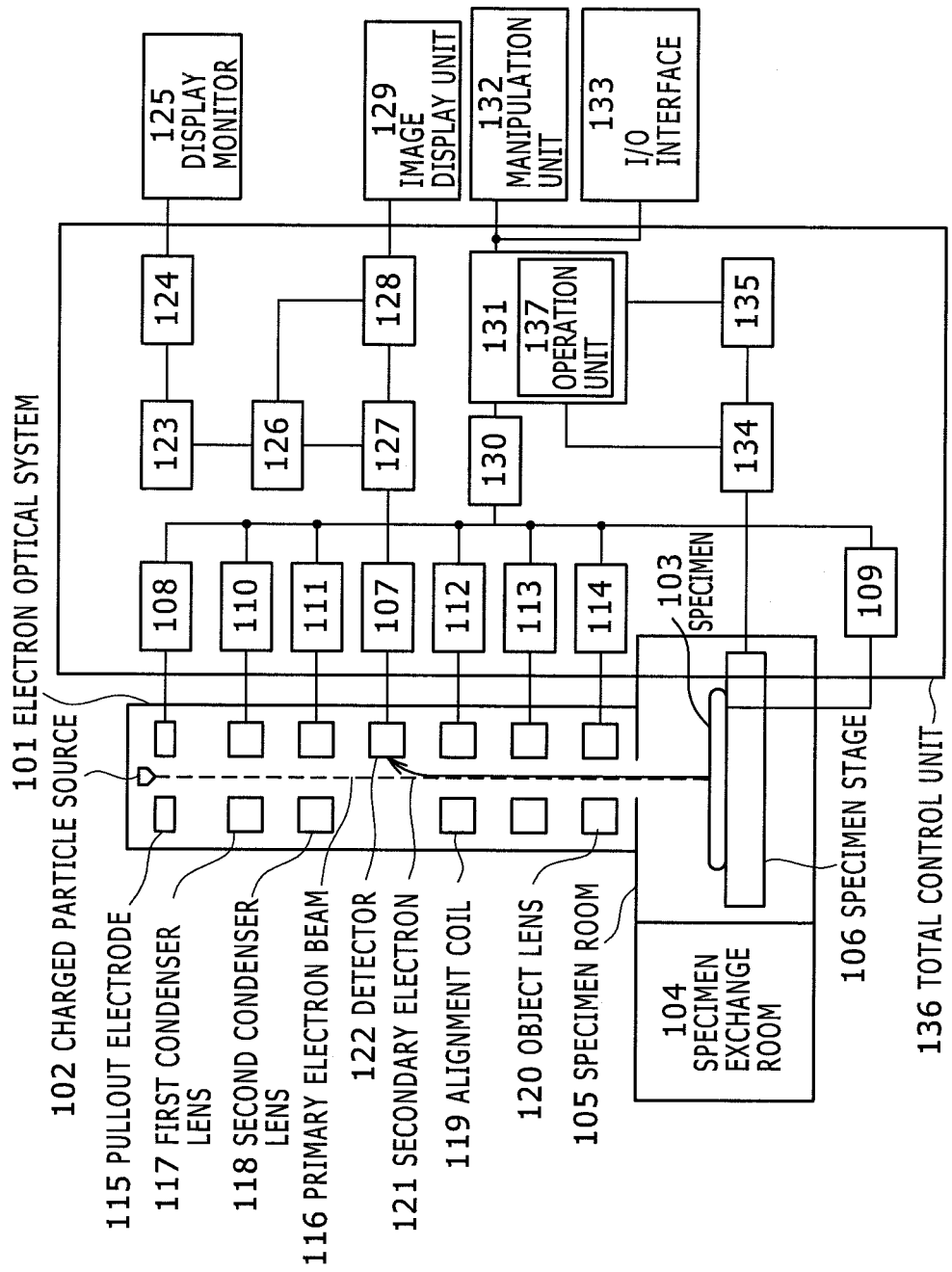
FIG. 1 is a schematic block diagram of a scanning electron microscope according to an embodiment of the present invention.

FIG. 1 is a schematic block diagram of a scanning electron microscope according to an embodiment of the present invention.

FIG. 1 shows a scanning electron microscope having an electron optical system 101 and a charged particle source 102. In the scanning electron microscope, a device control unit 131 automatically detects defects via a delivery control unit 135, a stage control unit 134, an electron optical system control unit 130, and an image processing control unit 127 on the basis of information about the position coordinates of defect candidates and inspection conditions that are input via a manipulation unit 132, or an I/O interface 133; and an automatic defect classification control unit (ADC) 124 classifies defect types on the basis of the detected images of the defects. Here, although the position coordinates of defect candidates are usually input via the I/O interface 133 after being examined by an external inspection device in advance, it is alternatively conceivable that the position of an observation target is manually input.

When inspection information about the coordinate position of each defect candidate, electron optical conditions and the like are input, the device control unit 131 issues specimen delivery instructions to the delivery control unit 135, so that a specimen 103 is delivered to a specimen stage 106 in a specimen room 105 via a specimen exchange room 104, and the specimen 103 is fixed on the specimen stage 106. The stage control unit 134 controls the specimen stage 106 to adjust the coordinates of the defect candidate on the basis of the coordinate position of the defect candidate sent from the device control unit 131 so that an electron beam can be accurately scanned. The electron optical system control unit 130 controls a high voltage control unit 108, a retarding voltage control unit 109, a first condenser lens control unit 110, a second condenser lens control unit 111, an alignment control unit 112, a deflecting current control unit 113, and an object lens control unit 114 on the basis of electron optical system conditions such as an acceleration voltage, a retarding voltage, and a photographing magnification sent from the device control unit 131 so that optimal electron beam scanning can be achieved. A primary electron beam 116 is pulled out from the charged particle source 102 by controlling a pullout electrode 115 via the high voltage control unit 108, and the primary electron beam 116 is axially adjusted by an alignment coil 119 after passing through a first condenser lens 117 and a second condenser lens 118. After passing through an object lens 120, the primary electron beam 116 is converged owing to the operations of the above optical lenses, so that the primary electron beam 116 is scanned with the coordinate position of the defect candidate on the specimen 103 as the scanning center. When the primary electron beam 116 is scanned on the specimen 103, a secondary electron beam 121 that is generated from the surface of the specimen 103 is captured by a detector 122, and the detected secondary electron beam is amplified by an amplifier 107 as an electric signal. The image processing control unit 127 converts the amplified electric signal into luminance information, and stores the luminance information in an image memory 126 as a photographed image. Subsequently, an image correction control unit 128 executes luminance correction processing on the photographed image, and the corrected photographed image is transferred to an image display unit 129, so that the photographed secondary electron image is displayed. In addition, after the photographed image of the defect candidate is stored in the image memory 126, a defect detection control unit 123 automatically judges whether the defect candidate is a defect or not on the basis of the photographed image, and if it is judged that the defect candidate is a defect, the photographed image is automatically transferred to the automatic defect classification control unit 124, and classification and analysis of the detected defect are performed, and the result is displayed on a display monitor 125. Hereinafter an assembly of the above mentioned control units are referred to as a total control unit 136. It goes without saying that the total control unit 136 includes other control units that are not shown. In addition, the total control unit 136 includes an operation unit 137, which executes operations regarding the behaviors of devices described later. The control units included in the total control unit 136 can be put into practice either by hardware or software, and further some of the control units can be put into practice in an all-in-one unit.

Figure 2:
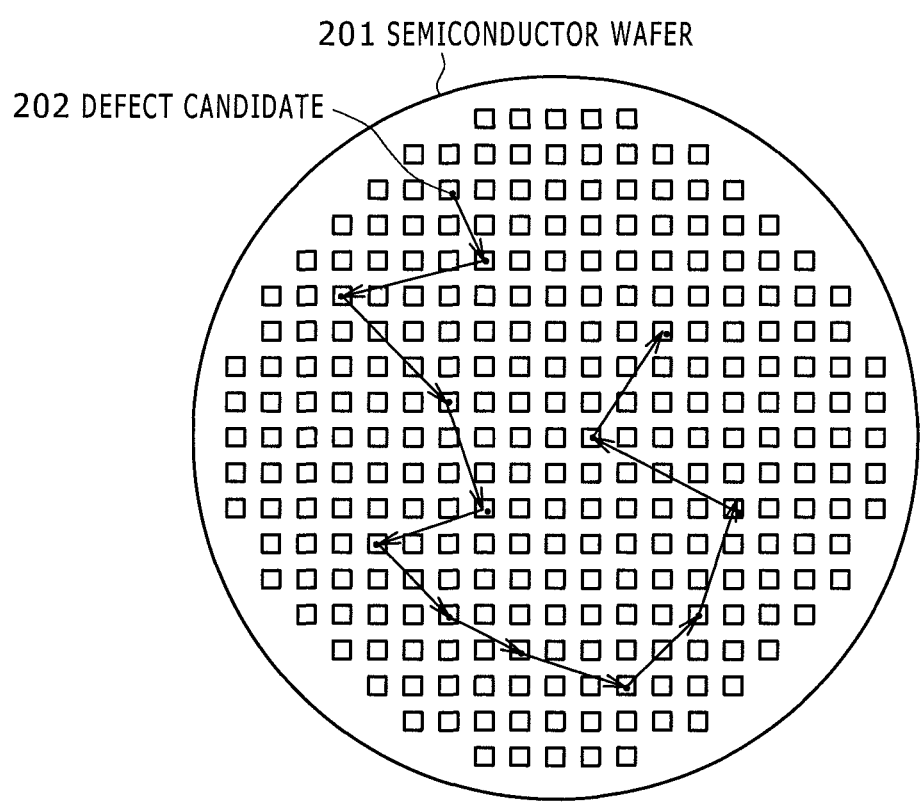
FIG. 2 is a diagram showing a stage transfer route on a specimen in the case where an ordinary automatic defect detection and a classification sequence are performed.

FIG. 2 is a diagram showing an example of a stage transfer route in the case where an automatic defect detection and a classification sequence are performed on an ordinary semiconductor wafer 201, and if a defect candidate 202 is an inspection start point, the automatic defect detection and the classification sequence for each defect candidate are performed in an order indicated by arrows. In most of automatic defect detections and classification sequences performed in semiconductor manufacturing lines, defects that are observation targets are automatically or manually selected (selecting automatically or manually will be referred to as sampling hereinafter) from defect candidates that are sporadically located at various areas on the surface of a specimen so that the defects can be detected in a well balanced manner at the respective areas on the basis of the input inspection information. In the sampling of defect candidates, a route that makes a stage transfer distance, which is dependent on the control by the stage control unit 134, minimum is derived by a fundamental algorithm, such as the Dijkstra algorithm and the Bellman-Ford algorithm, with the use of the coordinate positions of the defect candidates on the basis of inspection information so that the throughput for detecting defects may increase. This is because time required for the stage transfer occupies a large portion of time required for detecting one defect. (The reason that the route that makes the stage transfer distance minimum has to be derived is because time required for the stage transfer occupies a large portion of time for detecting one observation target.)

Figure 3A:
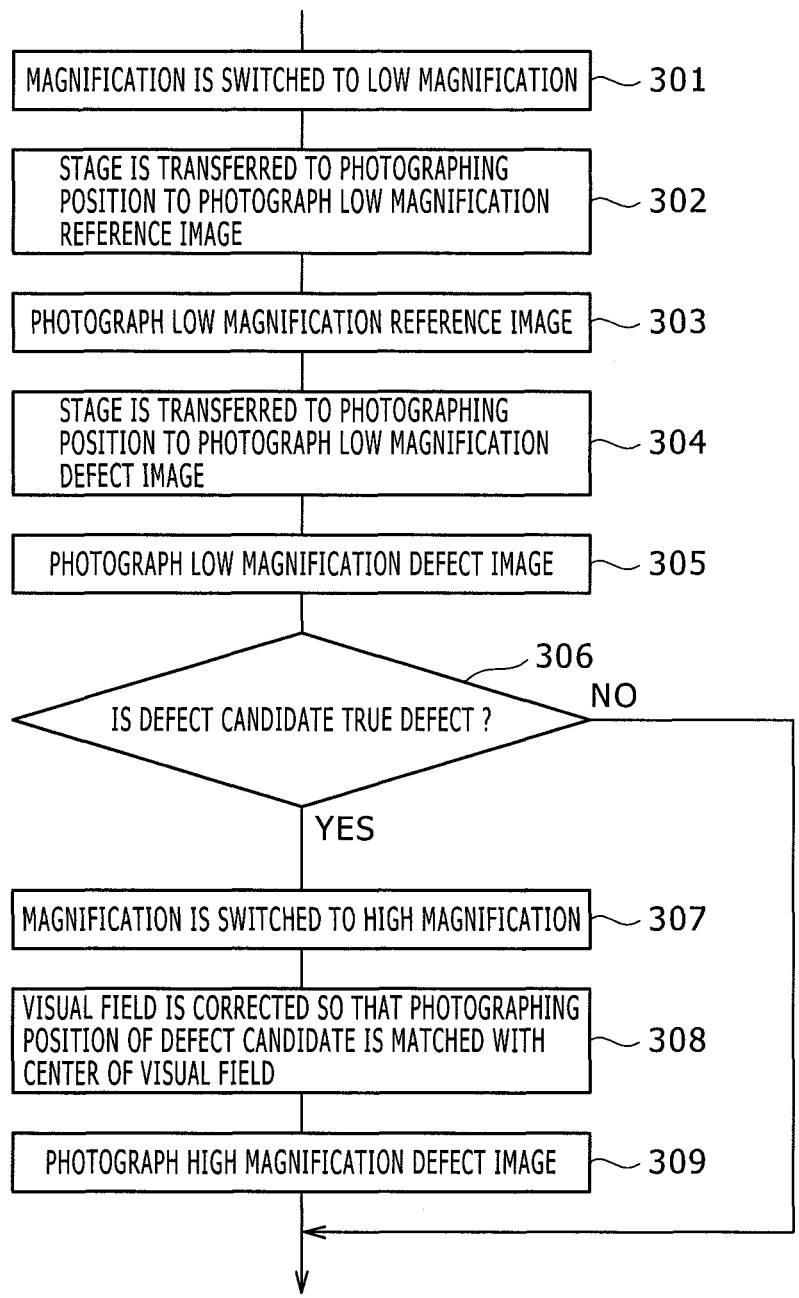
FIG. 3(a) is a flowchart of an ordinary detection sequence in the case where pre-charging is not executed.

Next, a flow of image photographing of one sampled defect candidate without using the pre-charge technology will be described with reference to FIG. 3(a). First, the photographing magnification is switched to a low magnification at step 301, and the stage is transferred to the coordinate position where a pattern, which is the same as that of the defect candidate, is formed on the specimen in order to compare the two patterns with each other at step 302. An image with which the defect candidate is compared is photographed at step 303 (This photographed image is referred to as a low magnification reference image hereinafter). Here, the switching the photographing magnification to a low magnification at step 301 can be executed in parallel with the stage transfer at step 302. Next, in order to photograph the image of the defect candidate (referred to as a low magnification defect image hereinafter), the magnification is kept intact, and the stage is transferred to the coordinate position of the defect candidate at step 304, and then the low magnification defect image is photographed at step 305. At step 306, the defect detection control unit 123 makes a defect judgment on the basis of the low magnification reference image and the low magnification defect image. In the case where the defect candidate is judged to be a true defect, because a defect image photographed at a high magnification (referred to as a high magnification defect image hereinafter) is needed in order for the detailed observation of the defect to be easily done, the low magnification is switched to a high magnification at step 307, a visual field correction is made so that the center of the visual field is matched with the center position of the photographing view field at step 308, and the high magnification defect image is photographed at step 309. If the defect detection control unit 123 judges that the defect candidate is not a true defect, steps after step 306 are omitted. Although it is not shown in FIG. 3(a), if the defect candidate is judged to be a true defect, the photographed image is transferred to the automatic defect classification control unit 124, and the defect is classified.

In the case where the detection and observation of the defect of a high aspect ratio portion such as a contact hole are performed, it is necessary to charge the surface of a specimen positively using the pre-charge technology. In addition, a saturation potential generated by the electron beam scanning in the pre-charging is a potential that forms a potential saddle point, and this potential saddle point depends on a pull-up voltage Ez and the electron beam irradiation area S, and the saturation potential is given by Equation (1), where a positively charge potential for pulling back a secondary electron is represented by α.

$$\text{Saturation Potential} = Ez \times \sqrt{S} + \alpha \qquad \text{Equation (1)}$$

Usually α is a several volt, and because the saturation potential mainly depends on the electron beam irradiation area S, when pre-charging is executed, photographing has to be executed after the magnification of electron optical system conditions is set low (desirable that the magnification is less than a thousand) and scanning an electron beam to a broad area with the center of the photographing view field as the scanning center to charge the area. This makes it possible to obtain a secondary electron image of the high aspect ratio portion. In addition, it goes without saying that there is a case where the specimen is charged negatively, if necessary. In other words, the present invention can be applied in both cases where the specimen is charged positively and negatively.

In the case where the pre-charge technology is used in the detection of one defect candidate, it is necessary that, after switching the electron optical system conditions to the pre-charging conditions, charge formation should be induced by scanning an electron beam for a certain period of time (this charge formation by scanning an electron beam for a certain period of time after switching the electron optical system conditions to the pre-charging conditions will be referred to as pre-charge processing hereinafter), and then the electron optical system conditions should be switched to normal image photographing conditions. Here, the above processing is executed three times as shown by step 310 in FIG. 3(b), that is, before photographing a low magnification reference image at step 303, before photographing a low magnification defect image at step 305, and before photographing a high magnification defect image at step 309. First, in order to cause the electron optical system conditions for pre-charging to generate an optimal charging effect, the photographing magnification is switched to a magnification lower than that of the low magnification image photographing so that the scanning area of the electron beam becomes broader at step 310. Next, in order to increase charge amount, a retarding voltage is raised by the retarding voltage control unit 109. In addition, in order to increase the amount of the primary electron beam 116 that is used for scanning the surface of the specimen 103, and increase the charge density, a first condenser lens current C1 is controlled by the first condenser lens control unit 110 to cause the amount of the electron beam that passes through an aperture (not shown) to be increased. The above mentioned optical conditions used in the pre-charging, such as the retarding voltage condition will be referred to as pre-charging conditions. Because pre-charging is a process for inducing the charge formation, and it is necessary that the electron optical system conditions for pre-charging have to be switched back to the electron optical system conditions for photographing when an image is photographed, the electron optical system conditions and the like have to be changed from the pre-charging conditions to the image photographing conditions.

Total time PT required for pre-charging execution at step 310 can be given Equation (2) if time for setting the electron optical system conditions for pre-charging is represented by PS, time for scanning the electron beam for a certain period of time by PA, and time for changing the electron optical system conditions for pre-charging to the electron optical system conditions for photographing by PB.

$$\text{Total time PT required for pre-charging execution} = PS \times 3 + PA \times 3 + PB \times 3 \quad \text{Equation (2)}$$

As shown by Equation (2), if grouping processing according to the present invention is not used, in the case where a defect candidate is a true defect, the pre-charging time required for the defect is required three times before photographing a low magnification reference image, before photographing a low magnification defect image, and before photographing a high magnification defect image.

Here, the charging speed (dV/dt) can be represented by Equation (3), where IP is a probe current, β is the secondary electron emission coefficient, and C is an electric capacitance that depends on the dielectric constant of the specimen.

$$dV/dt \propto IP \times (1-\beta)/C \quad \text{Equation (3)}$$

Because the charging speed becomes large as the probe current increases, the speed to reach the saturation potential linearly increases. Because the electric capacitance varies depending on the electron optical system conditions and the material of the specimen, time required by PA is not constant, and varies depending on various conditions.

In the area where defect candidates are densely located, if charge control is executed using a conventional pre-charge technology, the pre-charge scanning areas for the defect candidates overlap each other because the defect candidates are extremely near to each other, hence the electron beam scanning used in the charge control is executed repeatedly in some areas. In such a case, if the inspection sequence is repeatedly performed in an area, there is a possibility that the charge potential on the surface of a specimen exceeds the dielectric breakdown voltage although this possibility depends on various conditions such as types of specimens (oxide film and the like), thicknesses of insulation films, and the like, hence the dielectric breakdown occurs in the area where the electron beam scanning is executed repeatedly. In such a case, there is a method in which a part of the inspection sequence is skipped (for example, pre-charging is not executed) in the inspection sequence regarding a defect candidate if there is a possibility that the dielectric breakdown voltage is exceeded, and the inspection sequence regarding the next defect candidate is performed, and if the dielectric breakdown voltage is not exceeded, the execution of the inspection sequence is continued. Alternatively, there are some workarounds such as a first one in which the execution of the inspection sequence is suspended for a certain period of time because a charge potential on the surface of a specimen induced by electron beam scanning decreases with time; a second one in which known electricity removal processing with the use of ion irradiation, etc. is executed; and a third one in which the electron optical system conditions are changed to reduce charging efficiency so that the dielectric breakdown voltage is not exceeded.

However, each of the above mentioned workarounds has one or more problems in that throughput seriously decreases, it is necessary to mount dedicated hardware devices, or the defect detection rate decreases owing to an insufficient potential contrast.

These problems will be described with reference to FIG. 4.

Figure 4:
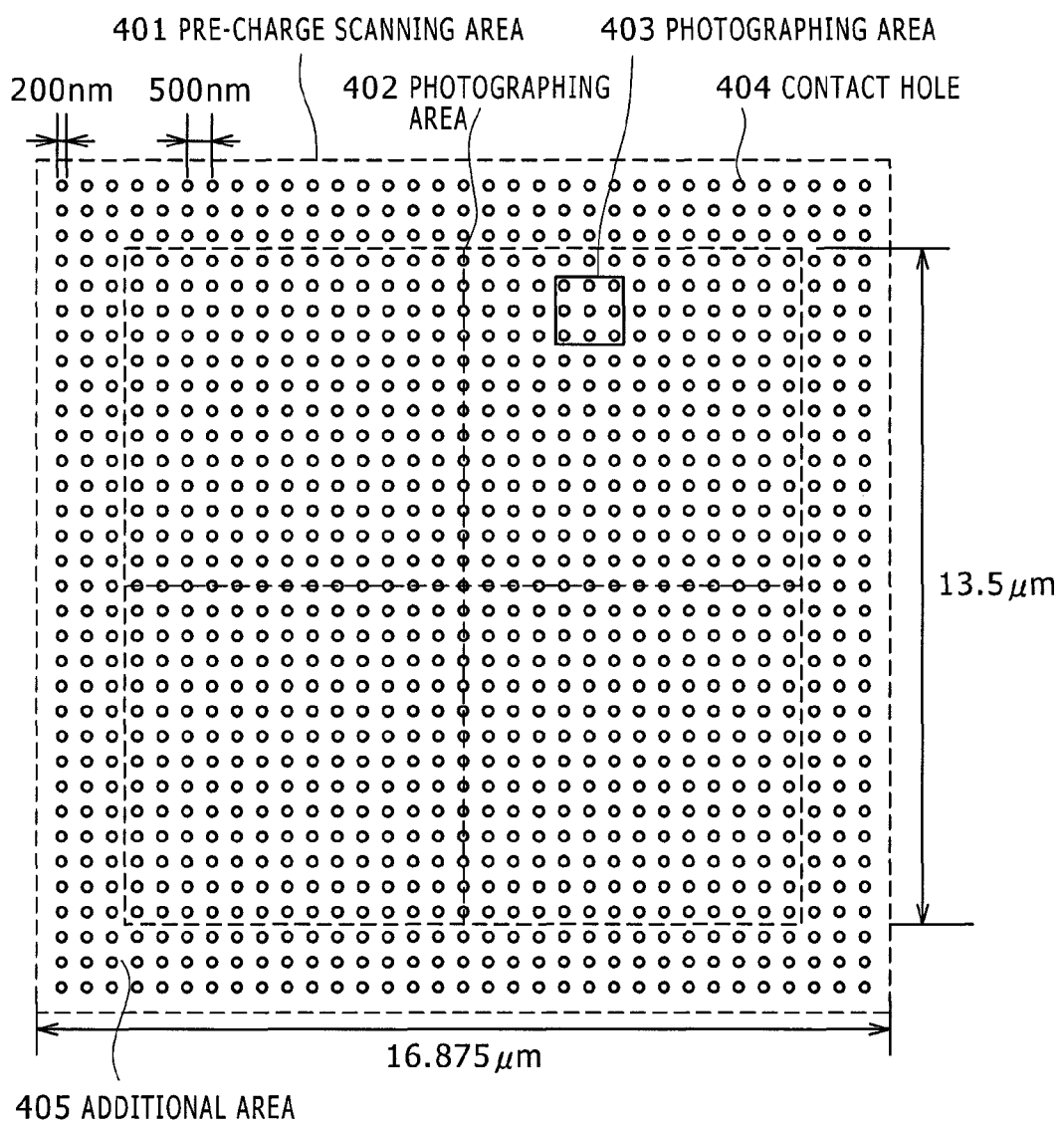
FIG. 4 is a diagram schematically showing a pre-charge scanning area and an image photographing area on a specimen.

FIG. 4 is a drawing showing an example of a specimen in which there are a pre-charge scanning area 401 and an electron beam scanning area where image photographing is executed at a low magnification that is a thousand magnification (hereinafter, referred to as a photographing area 402 of a low magnification image), and the pattern formation of contact holes 404 is made uniformly in both vertical and lateral directions in the photographing area 402.

If it is assumed that the diameter of each contact hole formed on the surface of the specimen is 200 nm, the distance between the centers of two adjacent contact holes is 500 nm, and the magnification of image photographing is a thousand, the effective display area (Field of View, referred to as an FOV hereinafter) for the photographing area 402 of the low magnification image is 13.5 µm square in the case of the display area of the image display unit 129 being 135 mm×135 mm. If pre-charging is executed on the area larger than the photographing area 402 of the low magnification image by 25% by extending the photographing area 402 uniformly in the left, right, top and bottom directions in order to make the photographing area 402 a stably charged area, the pre-charge scanning area 401 becomes 16.875 µm square. In such a way as above, adding an area to the photographing area (the area added to the photographing area will be referred to as an additional area 405 hereinafter) and executing charge control makes it possible that the entirety of the photographing area 402 is stably charged.

Although an example of a pre-charge scanning area with a low photographing magnification being a thousand has been taken in the above description, there is often a case where a low photographing magnification becomes larger in association with the miniaturization of observation targets. In the case where a low magnification is ten thousand, a photographing area 403 becomes 1.35 µm square. In recent defect detection relevant to a high aspect ratio portion, there is sometimes a case where the diameter of a contact hole is less than 50 nm, therefore the photographing magnification of a low magnification defect image becomes more than 50 thousand, and the photographing magnification of a high magnification defect image becomes more than 200 thousand, hence the photographing area of the high magnification image is displayed as if it were a small point.

If pre-charging is executed under the conditions shown in FIG. 4, 1089 (=33×33) contact holes are included in the pre-charge scanning area, so if there is a defect candidate in each contact hole, and automatic defect inspection and classification have to be performed, some areas are scanned more than several hundred times by an electron beam in pre-charging. In addition, there is a case where it is necessary to form a charged state which induces a voltage near to a dielectric breakdown voltage in some high aspect portions in order to obtain a potential contrast clear enough to detect defects, with the result that breakdowns may occur in areas which are scanned several hundred times by an electron beam.

Therefore, in a typical defect inspection and a classification sequence relevant to a high aspect ratio, if a continuous inspection sequence with the use of pre-charge technology is performed, it is necessary to pay attention so that the charge amount on the surface of a specimen does not exceed a dielectric breakdown voltage by giving priority to the nondestruction of a specimen and decrease of damage to the specimen. For example, electron optical system conditions nonoptimal for observation such as a condition to suppress a charging effect by lowering a retarding voltage have to be set, which naturally leads to the decrease of defect detection rate.

Accordingly, the invention according to the present application proposes pre-charge processing that decreases the risk of dielectric breakdown while maintaining a charging effect.

It is well-known that a charging effect induced by pre-charging in a defect inspection relevant to a high aspect ratio lasts for several tens of seconds to several hours depending on specimen conditions such as the material of the specimen, the thickness of an insulating film, and the density of a high aspect ratio structure, and an electron optical system condition. Here, if time required for detecting one defect (including time required for photographing a low and high magnification images and time required for switching optical conditions) is represented by m second, and the duration of the charging effect by n second, defect detection processing for detecting at least n÷m defects (wherein n÷m is the number of the defects) can be performed at a piece of pre-charging. Therefore, if the condition n>m is satisfied, it is conceivable that pre-charge processing is executed before photographing a low magnification image, and that the low magnification image and the high magnification image are photographed in a charged state formed by this pre-charge processing. As described above, two pieces of charge processing that are redundantly executed on the same portion can be replaced with a piece of charge processing, hence the risk of dielectric breakdown is decreased. In addition, if n and m satisfy conditions n>m and (n÷m)≥2, the inspection sequence for at least two defect candidates can be performed during time when the charging effect brought about by a piece of pre-charging is persistent. If the coordinate positions of defect candidates are near to each other, and pre-charge scanning areas are overlap each other, that is, if n and m satisfy conditions n>m and (n÷m)≥2 even when stage transfer times are included in n, plural defect candidates, which are located near to each other so that they can be pre-charged at the same time, can be classified into one group (classifying defect candidates into a group will be referred to as grouping the defect candidates hereinafter). Because the risk of dielectric breakdown can be removed, and optimal electron optical system conditions can be set by executing pre-charging on defect candidates grouped into one group, the defect detection rate is improved, and because the number of pre-charging executions made before defect photographing can be reduced, the throughput of defect detection is also improved.

In addition, when it comes to the duration n seconds of the charging effect, it is thinkable for an operator to input the value of the duration of the charging effect via a GUI, or for the value of the duration of the charging effect to be automatically estimated when the operator inputs a type of specimen to be used under the condition that a database including the reference values of charging effects corresponding various types of specimens is stored in advance.

hereinafter, two embodiments will be described: a first embodiment is an embodiment in the case where two conditions n>m, and (n÷m)≥2 are satisfied; and a second embodiment is an embodiment in the case where a condition n>m is satisfied.
First Embodiment As a first embodiment, an example of a grouping method in a pre-charge scanning area will be described hereinafter.

Figure 5:
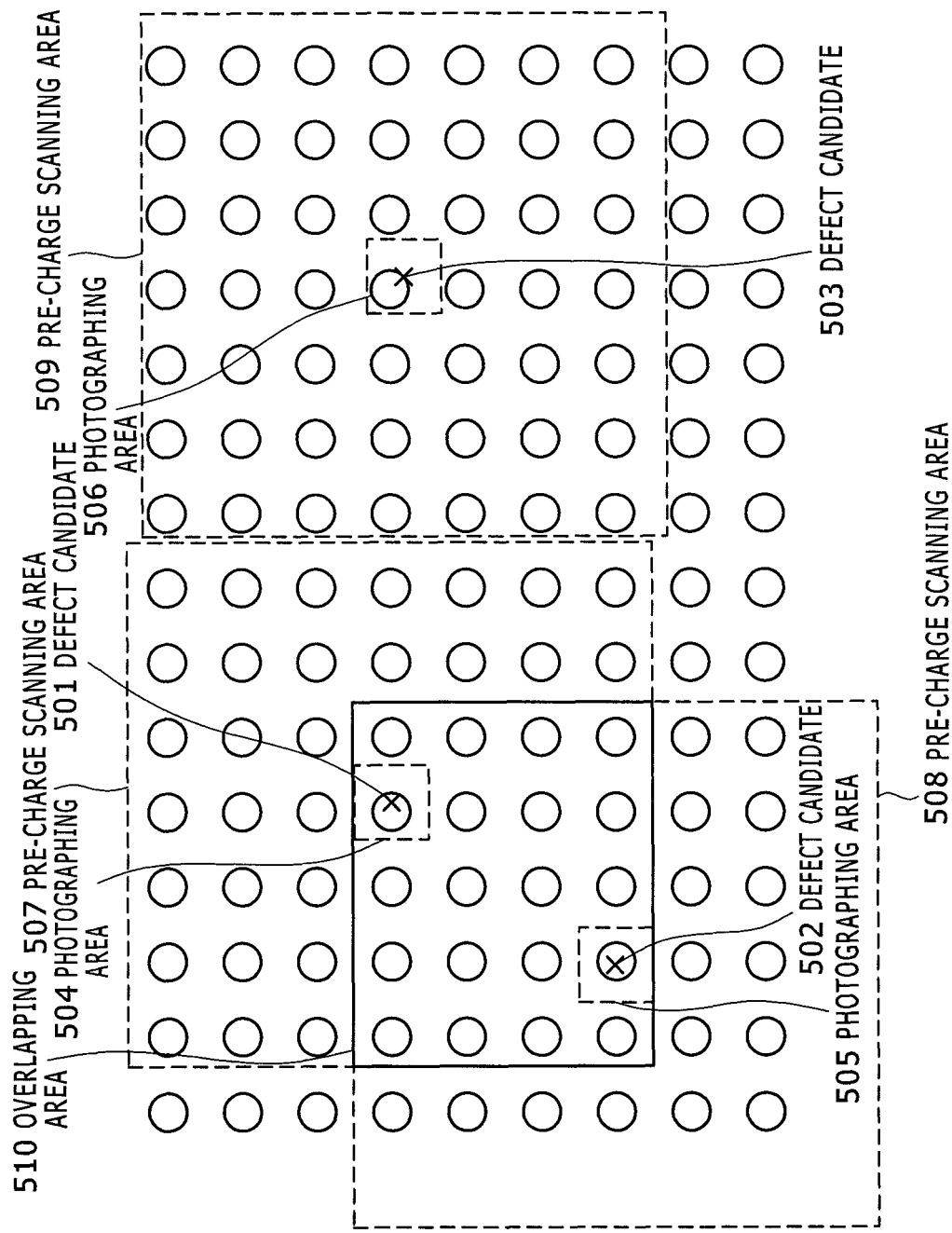
FIG. 5 is a diagram schematically showing three pre-charge scanning areas and three image photographing areas for three defect candidates.

FIG. 5 shows a fundamental concept about grouping according to the present invention and a method thereof. It will be assumed that a defect candidate 501, a defect candidate 502, and a defect candidate 503 are sampled in this order; the photographing area and the pre-charge scanning area of the low magnification image of the defect candidate 501 are respectively denoted by 504 and 507; the photographing area and the pre-charge scanning area of the low magnification image of the defect candidate 502 are respectively denoted by 505 and 508; and the photographing area and the pre-charge scanning area of the low magnification image of the defect candidate 503 are respectively denoted by 506 and 509.

First, it will be assumed that the lateral length and longitudinal length of the pre-charge scanning area are respectively denoted by Px and Py, and the lateral length and longitudinal length of the photographing area are respectively denoted by Zx and Zy, and it is judged whether each pre-charge area is included in one pre-charge scanning area or not with the use of the coordinate position of the defect candidate 501 (X1, Y1) and the coordinate position of the defect candidate 502 (X2, Y2). Here, the defect candidate 501 and the defect candidate 502 have been selected in the sampling order. If an additional area for stabilizing the charged state is ignored, this can be judged using the value Xa relevant to the lateral length and the value Ya relevant to the longitudinal length given respectively by Equation (4) and (5).

$$Xa=|X1-X2|+Zx \quad \text{Equation (4)}$$

$$Ya=|Y1-Y2|+Zy \quad \text{Equation (5)}$$

When Xa and Px are compared with each other, and Ya and Py are compared with each other, if Xa is equal to or smaller than Px, and Ya is equal to or smaller than Py, there is an overlapping area 510 (the area surrounded by solid line segments) for the defect candidate 501 and the defect candidate 502.

If it is necessary to take an additional area for stabilizing the charged state into consideration, the lateral length and longitudinal length of the additional area have only to be added to the right-hand sides of Equations (4) and (5) respectively. When it comes to the size of an additional area for stabilizing the charged state, because the distribution of charge potential varies depending on electric conductivities, which are determined by the material of a specimen and the thickness of an insulating film, an electron optical system condition, and the like, it is recommendable that a parameter that determines the size of the additional area can be changed as an input inspection condition by handling the parameter on a screen. In addition, it is conceivable that, with reference to various sizes of additional areas obtained in advance through measuring the distribution changes of charge potentials owing to the differences between conditions of inspection targets such as materials or thicknesses of specimens, an additional area corresponding to a specific observation target is automatically determined.

As can be seen in FIG. 5, because it can be judged that there is the area 510 where parts of the two pre-charge scanning areas overlap each other as described above, the defect candidate 501 and the defect candidate 502 belong to a common group. Next, it will be judged whether the above group include a defect candidate other than the above two defect candidates or not. First, a judgment relevant to the defect candidates 501 and 503 will be made. In this case, as can be seen in FIG. 5, because there is no area where parts of two pre-charge scanning areas for the defect candidates 501 and 503 overlap each other, the defect candidate 501 and the defect candidate 503 do not belong to the same group. Next, a judgment relevant to the defect candidates 501 and 503 will be made. In this case, because there is also no area where parts of two pre-charge scanning areas for the defect candidates 502 and 503 overlap each other, the defect candidate 502 and the defect candidate 503 do not belong to the same group. As a result, only the defect candidate 501 and the defect candidate 502 are grouped into the same group because parts of the pre-charge scanning areas for the defect candidates 501 and 502 overlaps each other, and because any part of the pre-charge scanning area for the defect candidates 503 does not overlap any parts of the pre-charge scanning areas for the defect candidates 501 and 502, the defect candidate 503 is judged to be subject to pre-charging by itself.

The processing to group defect candidates that are charged all together as above is executed by the operation unit 137 set up in the total control unit 136. The operation unit 137 can be installed by either hardware or software, or it can be installed in combination with other control units.

Figure 6:
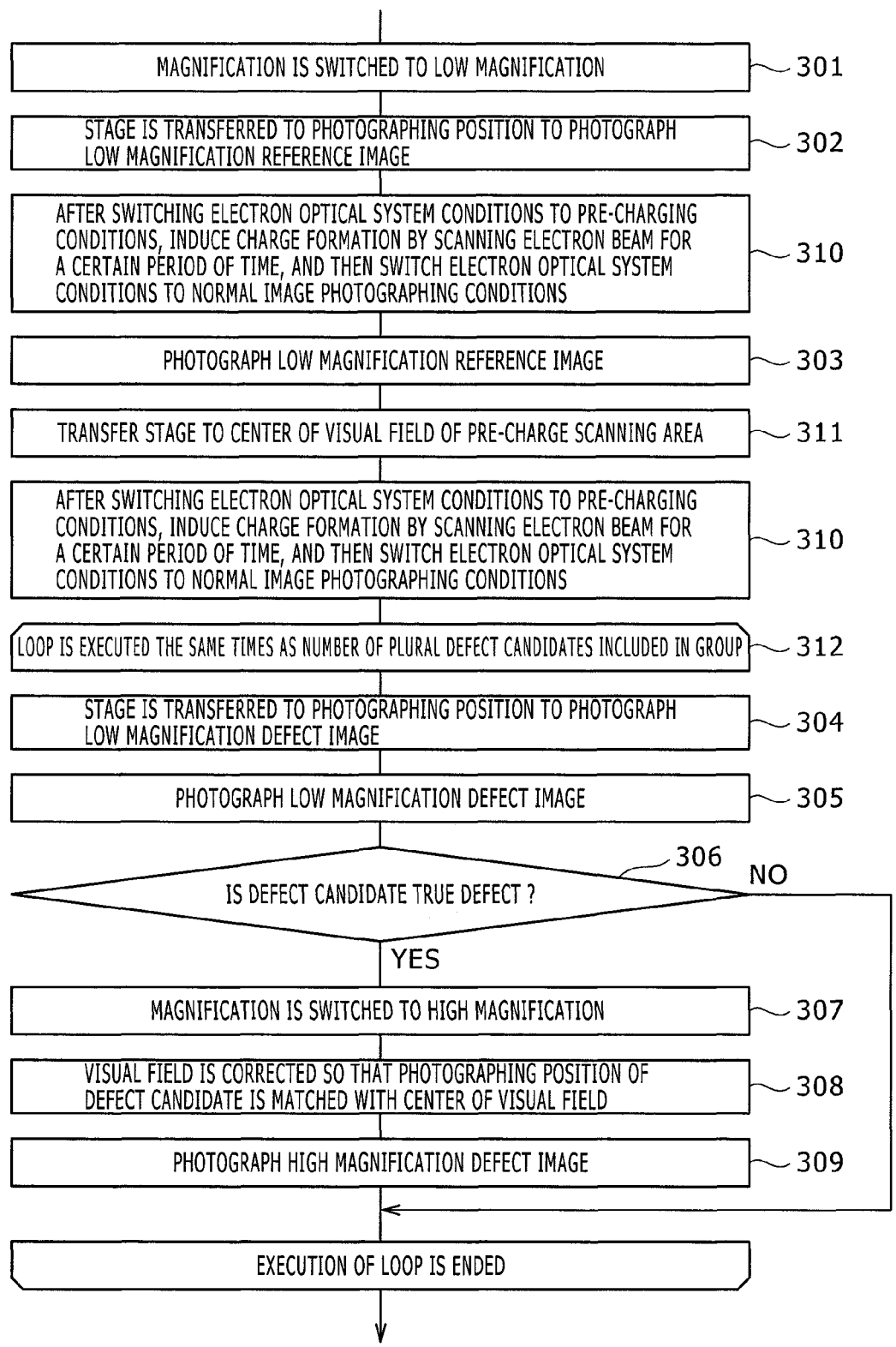
FIG. 6 is a flowchart of a detection sequence in the case where pre-charge scanning areas are grouped.

FIG. 6 shows a flow of defect observation conducted in the above grouping. In other words, if it is judged that the number of pre-charging executions in this case can be reduced than that in FIG. 3(b) by the operation unit 137, the flow becomes a flow shown in FIG. 6.

The flow shown in FIG. 6 is the same as the flow shown in FIG. 3(b) from step 301 to step 303, but after the stage is shifted to the center of the visual field of the pre-charging scanning area in FIG. 6 at step 311, pre-charging is executed in common for photographing low magnification defect images and high magnification defect images of plural defect candidates included in the pre-charging scanning area at step 310. Next, at step 312, a loop number is set equal to the number of plural defect candidates included in the pre-charge scanning area, and the flow from step 304 to step 309 is repeated the same times as the loop number. At step 306, if each defect candidate is judged not to be a true defect, or if each defect candidate is judged to be a true defect, the following steps are respectively executed as described above. As described above, a defect image and a high magnification image can be photographed after a piece of pre-charging. In addition, plural images relevant to plural defect candidates can be photographed by a piece of pre-charging, hence the pre-charge scanning areas are prevented from overlapping each other and dielectric breakdown can be effectively avoided. In addition, because the number of pre-charging executions can be decreased without decreasing the detection sensitivity, time required for pre-charging can be decreased and the throughput is improved.

Figure 7:
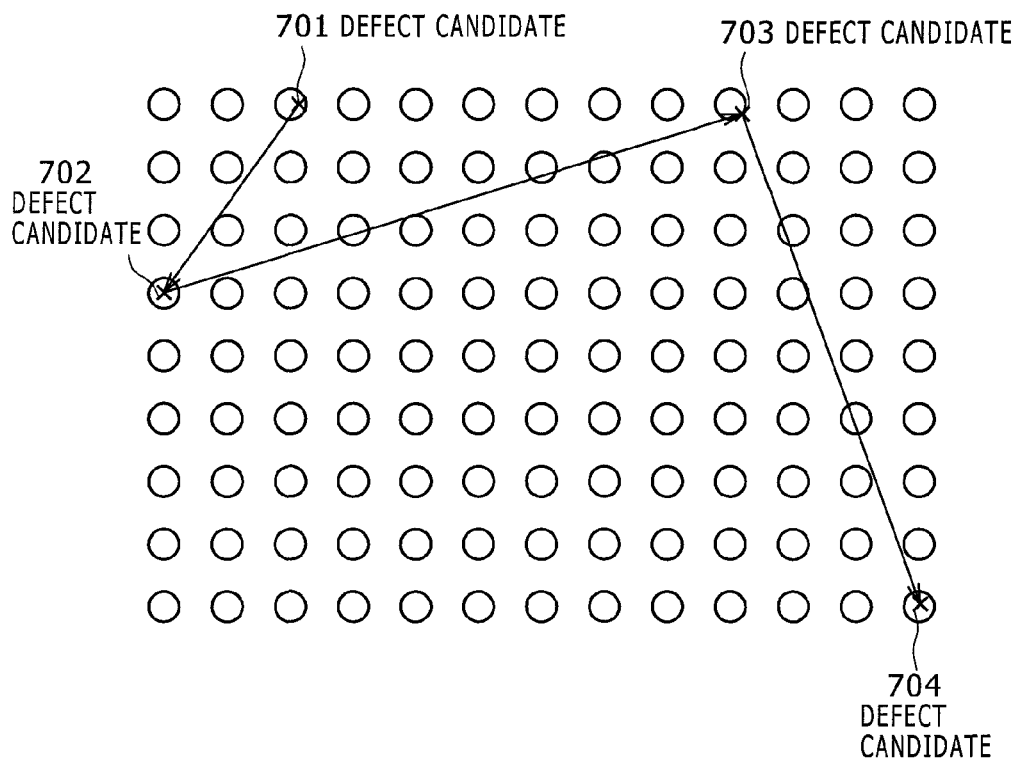
FIG. 7 is a diagram schematically showing a sampling order that minimizes a stage transfer route.

Next, the execution order of the grouping judgment processing, and the end judgment of the grouping processing relevant to one group will be described with reference to FIG. 7. In FIG. 7, it will be assumed that defect candidates 701, 702, 703, 704, and others (not shown) are sampled and these defect candidates are on a route that starts from the defect candidate 701 and provides the shortest stage transfer distance. After it is determined that the defect candidate 701 and the defect candidate 702 can belong to the same group, it is judged whether the defect candidate 703 can belong to the group to which the defect candidates 701 and 702 belong or not. If it is judged that the defect candidate 703 cannot belong to the group to which the defect candidates 701 and 702 belong, it is unnecessary to judge whether the defect candidate 704 and others following the defect candidate 704 can belong to the group to which the defect candidates 701 and 702 belong or not, because the defect candidate 704 and others following the defect candidate 704 are located farther from the group to which the defect candidates 701 and 702 belong than the defect candidate 703 is located. Therefore, grouping judgment relevant to the group to which the defect candidates 701 and 702 belong is finished, and it is decided that this group includes only the defect candidate 701 and the defect candidate 702. Next, it is judged whether the defect candidate 703 and the defect candidate 704 can belong to the same group or not. If it is judged that the defect candidate 703 and the defect candidate 704 cannot belong to the same group, the defect candidate 703 is not grouped with any defect candidate, and pre-charging is executed only on the defect candidate 703. After this, it is judged whether the following defect candidates can be grouped or not in the sampling order. When the judgment on the last defect candidate is finished, the grouping relevant to pre-charging is finished.

Although it depends on an algorithm used for the sampling, it seems to take time for the grouping relevant to pre-charging to be finished if defect candidates are not sampled along a route that makes the stage transfer distance the shortest, or if distances between adjacent defect candidates do not get larger in the sampling order although the defect candidates are sampled along the route that makes the stage transfer distance the shortest. However, the grouping relevant to pre-charging ends when the grouping judgment is made on all the defect candidates in the sampling order and the last defect candidate undergoes the grouping judgment.

The above described grouping processing can be executed independently of the sampling after defect candidates that become observation targets are determined among all the defect candidates and sampling processing that makes the stage transfer distance the shortest is finished. In the above case, if the shortest route of the stage transfer is calculated again after the grouping relevant to the last defect candidate is finished on the basis of the coordinate position of the center of the view field of the pre-charge scanning field of each group, and the coordinate position of each defect candidate only on which the pre-charging is executed, this is helpful in improving the throughput of the inspection sequence. On the other hand, if an algorithm that executes grouping at the time of sampling is adopted, the sampling is finished when the grouping is finished on the last defect candidate, so there is no need to execute the sampling again.

Next, setting of the center of the view field of a pre-charge scanning area will be described. If there is only one defect candidate in a pre-charge area as is the case with the defect candidate 503 in the pre-charge area 509 shown in FIG. 5, pre-charging can be executed with the center of the view field being the coordinate position of the defect candidate 503, but if plural defect candidates are included in a group, it is necessary to decide the center of the view field of a pre-charge scanning area. A scanning area setting unit decides setting of the center of the view field of a pre-charge scanning area with the use of methods described later with reference to FIG. 8 to FIG. 12 while taking a potential barrier and a charging effect induced by pre-charging into consideration. Although the scanning area setting unit is not shown in FIG. 1, the scanning area setting unit can be included, or can be installed by itself, and can be installed by either hardware or software.

Figure 8:
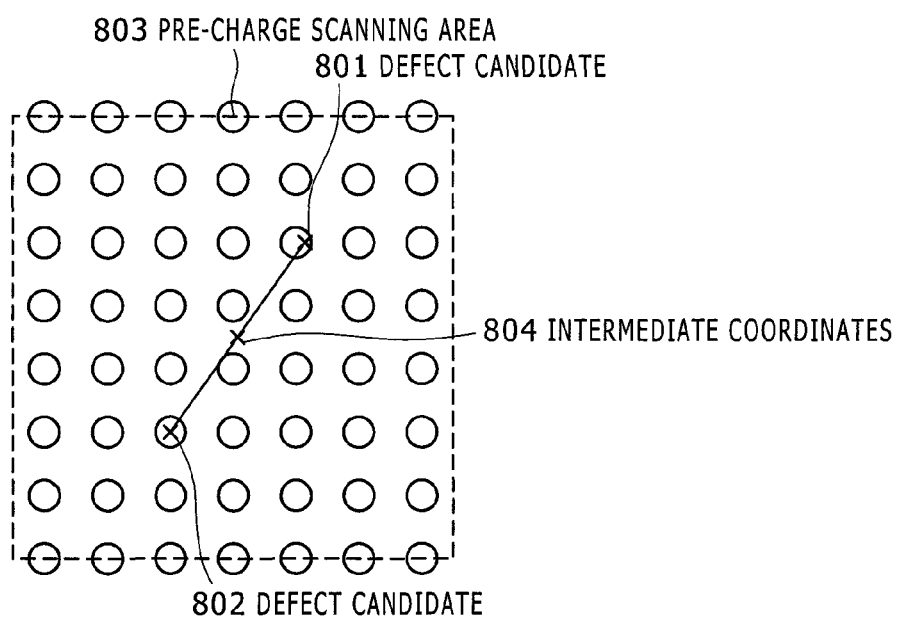
FIG. 8 is a diagram schematically showing the center of a pre-charge scanning area in the case where two defect candidates are grouped.

Hereinafter, concrete setting and correction method of the center of the view field of a pre-charge scanning area will be described. In the case where a defect candidate 801 and a defect candidate 802 are grouped and pre-charging is executed on these defect candidates all together as shown in FIG. 8, pre-charging can be executed in a pre-charge scanning area 803 with the center of its view field being the intermediate coordinates 804 of the coordinates of the two defect candidates so that the charge states in the vicinities of the coordinate positions of both defect candidates become optimal.

In this case, if charge formation is made by pre-charging, although it depends on the material of a specimen and electron optical system conditions, there is concern that a potential barrier is formed in the vicinity of the border between pre-charge scanning areas, necessary charge is not formed in the vicinity, and an abnormal contrast occurs owing to the nonuniform charge distribution.

Figure 9A:
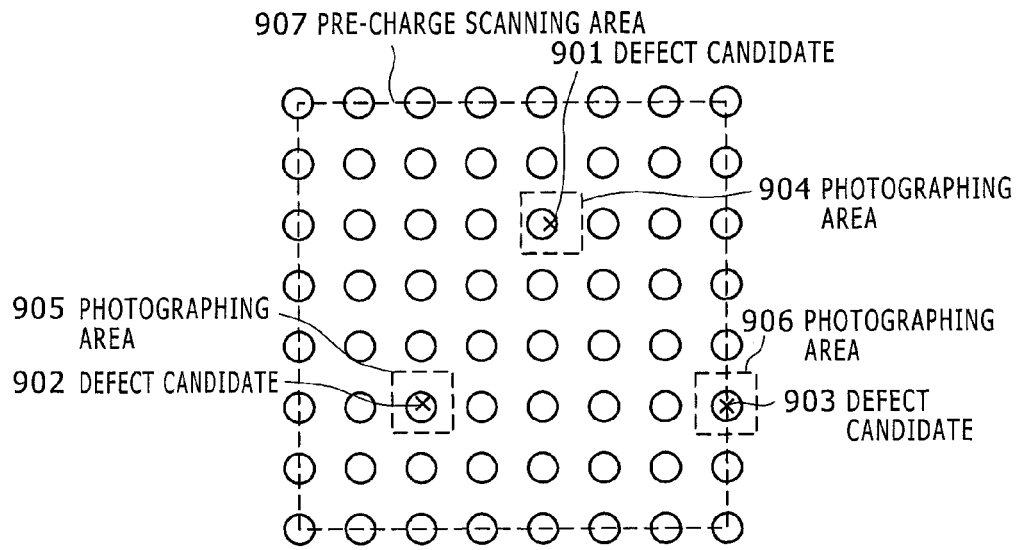
FIG. 9(a) is a schematic diagram in the case where the photographing area of a defect candidate is located in the vicinity of a potential barrier.

The above will be described with reference to FIG. 9(a). In FIG. 9(a), it will be assumed that defect candidates 901, 902, and 903 are grouped together; the photographing area of the defect candidate 901 is denoted by 904; the photographing area of the defect candidate 902 by 905; the photographing area of the defect candidate 903 by 906; and the photographing area 906 of the defect candidate 901 is located on the border of a pre-charge scanning area 907 and in the vicinity of an area where a potential barrier is generated. In the vicinity of the area where the potential barrier is generated, because the nonuniformity of a potential contrast is generated owing to the nonuniform charge, the secondary electron beam 121 is deflected by an electric field, and cannot be captured by the detector 122, which leads to a possibility that a defect cannot be detected accurately. Therefore, it is necessary to detach the photographing area from the vicinity of the potential barrier generated in the vicinity of the border of the pre-charge scanning area.

As a detaching method, there is a method in which an area that is apart inside from the border of the pre-charge scanning area by a constant distance α is set as an effective scanning area to remove the influence of the nonuniform charge distribution in the vicinity of the potential barrier, which is useful for the improvement of the defect detection rate.

Figure 9B:
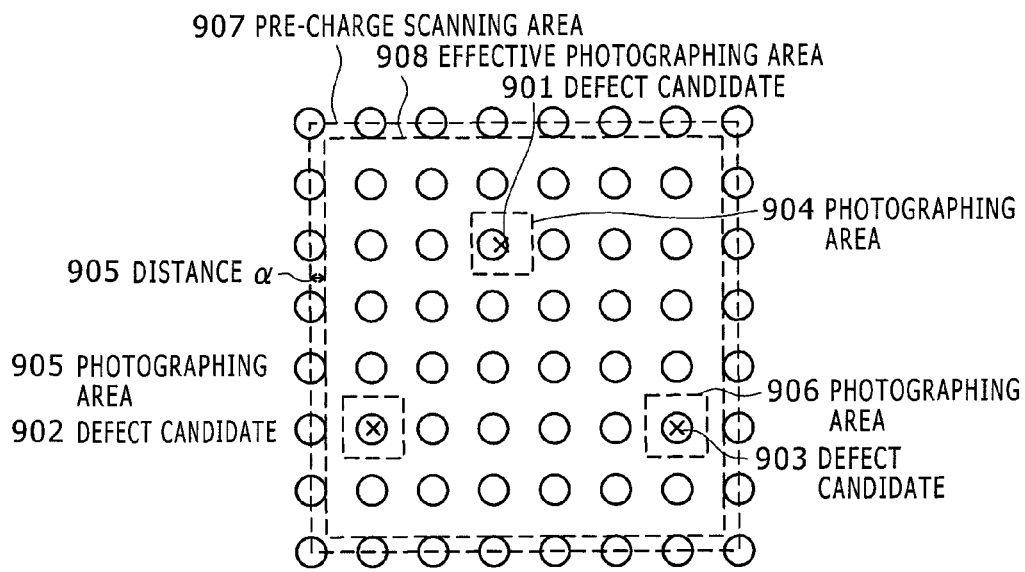
FIG. 9(b) is a schematic diagram in the case where the photographing area of a defect candidate is shifted within the photographing effective area of a pre-charge scanning area.

FIG. 9(b) shows an example of an effective photographing area apart inside from the border of the pre-charge scanning area shown in FIG. 9(a) by a constant distance. In FIG. 9(b), it is all right that an area apart inside from the border of the pre-charge scanning area 907 by a constant distance α 920 is set as an effective photographing area 908 so that the photographing area 906 of the defect candidate 903 is not located in the vicinity of the border of the pre-charge scanning area 907, and the center of the view field of the pre-charge scanning area is adjusted so that the photographing areas of all the defect candidates in the group are located within the effective photographing area 908.

If an area apart inside from the border of the pre-charge scanning area by a constant distance α 920 is set as an effective photographing area 908, the effective photographing area has only to be defined as the area whose border is apart inside from the border of the pre-charge scanning area by the constant distance α 920. In addition, because charging effect varies owing to the material of a specimen and electron optical system conditions, etc., it is more desirable that the distance α 920 can be changed using a GUI on a screen as an inspection condition in a similar way to the case of the size of an additional area for stabilizing a charge state. In addition, it goes without saying that it is conceivable that the value of the distance α 920 is set as a value that is a certain ratio of the size of the photographing area or the pre-charge scanning area. It is also conceivable that an photographing prohibited area in which photographing is prohibited is defined in the vicinity of the border of a pre-charge scanning area instead of the effective photographing area, and a rule is made the a defect candidate located in the photographing prohibited area is not photographed. If the effective photographing area is defined as a certain ratio of the photographing area, the effective photographing area can flexibly keep pace with the variation of the photographing area (the variation of the magnification).

In the case where charge formation is made with the use of a pre-charge technology disclosed in Patent Literature 1 (hereinafter referred to as one-step pre-charging), the charge potential is gradually lowered as the observation point of the charge potential is apart from the center of the view field of the pre-charge scanning area, that is, the distribution of the potential is not uniform in the pre-charge scanning area. On the other hand, described in Japanese Unexamined Patent Application Publication No. 2009-99540 is a technology in which, after charge formation is made by electron beam scanning, preliminary irradiation is executed with a different acceleration voltage to flatten the charge distribution (this technology will be referred to as two-step pre-charging hereinafter). In the case where charge formation made with the two-stage pre-charging, charge distribution in a pre-charge scanning area is flattened, the charge potential is kept over a certain level, and the charge distribution can be made uniform or almost uniform. Thinking of the above, in the case where the one-step pre-charging is used, a defect candidate having the photographing area near the center of the view field of the pre-charge scanning area can be photographed with excellent charging effect, so that a high quality image can be obtained, while a defect candidate having the photographing area far from the center of the view field of the pre-charge scanning area is photographed with deteriorated charging effect, so that such a defect candidate, being adversely affected by the deteriorated charging effect, will have a worse defect detection rate compared with the defect candidate having the photographing area near the center of the view field. On the other hand, in the case where the two-step pre-charging is used, the photographing areas of defect candidates can be located at anywhere as long as they are located within an effective photographing area 908. For example, there is no problem even if a photographing area 906 adjoins an effective photographing area 908 as shown in FIG. 9(c).

In the case where the one-step pre-charging is used, it is required in certain cases that the center of the visual field of a pre-charge scanning area is adjusted so that a defect is located in the vicinity of the center of the pre-charge scanning area. Judgment whether the correction of the center of the visual field of a pre-charge scanning area is necessary or not depends on the coordinate positions of the grouped defect candidates and a pre-charge technology to be used. If the coordinate positions are densely located in the vicinity of the center of the visual field of the pre-charge scanning area, the necessity of the correction of the center of the visual field of the pre-charge scanning area is low even in the case where the one-step pre-charging is used, while even if the coordinate positions are located in the vicinity of the border of the pre-charge scanning area, the correction of the center of the visual field of the pre-charge scanning area become unnecessary by using the two-step pre-charging.

It is conceivable that, after analyzing the coordinate positions of grouped defect candidates, switching from the one-step pre-charging to the two-step pre-charging or vise versa is made depending on the density of the grouped defect candidates. As described above, because the uniformity of charge can be achieved by adopting the two-step pre-charging depending on circumstances, the throughput can be improved. In addition, in accordance with the selection of the one-step pre-charging or the two-step pre-charging, the size of a pre-charge scanning area can be changed. In other words, the judgment of defects to be grouped can be changed. If the one-step pre-charging is selected as an inspection condition, because it is necessary to locate photographing areas near to the center of the view field of a pre-charge scanning area, the distance α 920 is made large, while if the two-step pre-charging is selected, because charge in the pre-charge scanning area is nearly uniform, the distance α 920 can be small, hence it becomes possible to group more defect candidates.

Figure 9C:
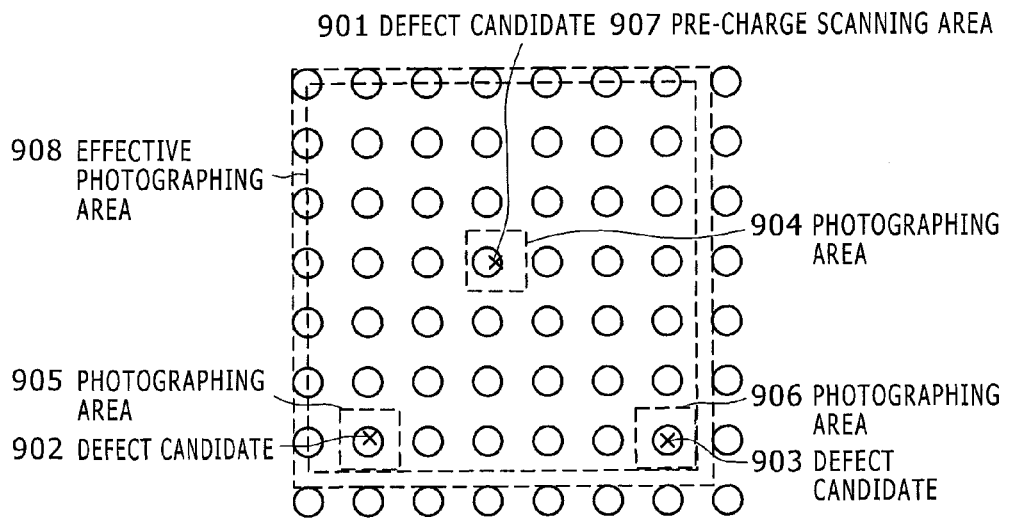
FIG. 9(c) is a schematic diagram in the case where the photographing area of a defect candidate is located very near to the photographing effective area of a pre-charge scanning area.
Figure 10:
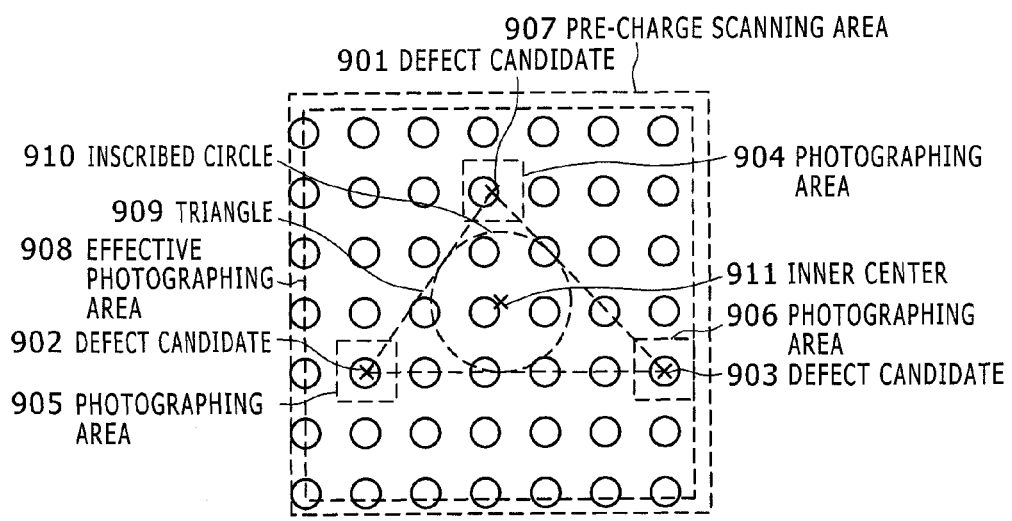
FIG. 10 is a diagram schematically showing the case where the inner center of a triangle having coordinate positions of three defect candidates as its vertices is set to be the center of the visual field of a pre-charge scanning area.

FIG. 10 shows an example of setting of the center of the view field shown in FIG. 9(c). The center of an inscribed circle 910 of a triangle with the coordinate positions of the defects as vertexes (the inner center 911 of the triangle) is calculated on the basis of the coordinate positions of the defect candidates shown in FIG. 9(c) by an operation unit (not shown), and the correction to set the calculated inner center 911 as the center of the view field of the pre-charge scanning area is executed.

In the case where there are three or more defect grouped candidates, if the above described correction method relevant to the center of the view field of a pre-charge scanning area is used, all the inner centers of triangles made with the use of the coordinate positions of the defect candidates as vertexes have to be calculated. Subsequently, after setting the coordinate position of each inner center as the center of the view field of the pre-charge scanning area, the coordinate position of an inner center that makes the photographing areas of all the defect candidates located within the effective photographing area can be adopted as the center of the view field. In this case, when the number of defect candidates in the group increases, it is expected that the coordinate positions of the defect candidates are nonuniformly located in the pre-charge scanning area. Even in such a case, the two-step pre-charging is more advantageous than the one-step pre-charging because the two-step pre-charging can make the potential distribution uniform or nearly uniform to the vicinity of the border of the effective photographing area.

A method for obtaining the center of the view field of a pre-charge scanning area in the case where a defect candidate is added to the three defect candidates shown in FIG. 10 so that there are four defect candidates in a group will be described.

If there are four defect candidates, four triangles are made with the use of the coordinate positions of the four defect candidates as vertexes. For example, the coordinate positions of four inner centers, that is, an inner center 911 of a triangle with the coordinate positions of defect candidates 901, 902, and 903 as its vertexes, an inner center 915 of a triangle with the coordinate positions of defect candidates 901, 902, and 918 as its vertexes, an inner center 916 of a triangle with the coordinate positions of defect candidates 902, 918, and 903 as its vertexes, and an inner center 917 of a triangle with the coordinate positions of defect candidates 901, 918, and 903 as its vertexes, are calculated by the operation processing unit.

Because the coordinate positions of the defect candidates are nonuniformly distributed, when the center coordinate position of the obtained inner center is set as the center of the view field of the pre-charge scanning area, there is a possibility that the photographing area of a certain defect candidate is located outside the effective photographing area. Therefore, it is necessary to determine the coordinate position of an inner center that makes all the photographing areas, that is, the photographing area 904 of the defect candidate 901; the photographing area 905 of the defect candidate 902; the photographing area 919 of the defect candidate 918; and the photographing area 906 of the defect candidate 903, located in the effective photographing area 908 on the basis of the obtained coordinate positions of the inner centers.

A method for determining the coordinate position of an inner center will be described taking the inner center 911 of the triangle with the coordinate positions of the defect candidates 901, 902, and 903 as its vertexes for example. It will be assumed that the coordinate position of the inner center 911 is (X, Y), the lateral length of the effective photographing area 908 is Zx, the longitudinal length of the effective photographing area 908 is Zy, the coordinate position of the defect candidate 901 is (Xa, Ya), the lateral length of the photographing area 904 is Zxa, the longitudinal length of the photographing area 904 is Zya in a coordinate system of a plane that has the coordinate position (X, Y) of the inner center 911 as its origin. In this coordinate system, if any of the following inequalities is satisfied, it is proved that the photographing area 904 of the defect candidate 901 is located in the effective photographing area 908.

$(X+(Xa+Zxa/2)) \leq (X+Zx/2)$ and $(Y+(Ya+Zya/2)) \leq (Y+Zy/2)$ if the coordinate position of the defect candidate is located in the first quadrant (Xa≥X, Ya≥Y);

$(X+(Xa-Zxa/2)) \leq (X-Zx/2)$ and $(Y+(Ya+Zya/2)) \leq (Y+Zy/2)$ if the coordinate position of the defect candidate is located in the second quadrant (Xa<X, Ya>Y);

$(X+(Xa-Zxa/2)) \leq (X-Zx/2)$ and $(Y+(Ya-Zya/2)) \leq (Y-Zy/2)$ if the coordinate position of the defect candidate is located in the third quadrant (Xa<X, Ya<Y); or $(X+(Xa+Zxa/2)) \leq (X+Zx/2)$ and $(Y+(Ya-Zya/2)) \leq (Y-Zy/2)$ if the coordinate position of the defect candidate is located in the fourth quadrant (Xa>X, Ya<Y).

If similar inequalities are satisfied respectively for the defect candidates 902 and 903 that are the remaining vertexes of the triangle with the inner center 911, it is proved that the photographing areas of all the defect candidates that are the vertexes of the triangle with the inner center 911 are located in the effective photographing area.

In the case where there are plural inner centers that satisfy the above condition, the optimal inner center is decided by the following procedures. First, after setting each inner center that satisfies the condition as the center of the view field of the pre-charge scanning area, distances between the defect candidates and the effective photographing area are measured taking the fact that, when one-step pre-charging is used, the nearer to the center of the view field the coordinate position of a defect candidate is, the clearer image optimally advantageously affected by a charging effect can be photographed into consideration. Next, by comparing the shortest distances relevant to the inner centers with each other, the coordinate position of the inner center having the shortest distance that is the largest of the above shortest distances is appointed as the center of the view field of the pre-charge scanning area. As a result, the defect candidates are more uniformly apart from the border of the effective photographing area. In other words, it is preferable that the inner center obtained as above is appointed as the center of the view field of the pre-charge scanning area. In the above method, the order for the operation unit to obtain the coordinate position of the center of the view field of the pre-charge scanning area after calculating the inner centers of the triangles with the coordinate positions as their vertexes can be random.

When two-step pre-charging is used, because a potential distribution can be made uniform or nearly uniform to the vicinity of the border of the effective photographing area, if the coordinate position of a certain inner center that is appointed as the center of the view field satisfies the above mentioned condition, the search of the center of the view field can be stopped at the time, and the coordinate position of the certain inner center can be appointed as the center of the view field.

With the use of the above described method, the center of the view field of the pre-charge area can be set, but in the case where the one-step pre-charging is used, the obtained charged state is not always an optimal charged state for defect candidates other than the defect candidates that are the vertexes of the triangle whose inner center is the center of the view field. Processing for such a case will be described hereinafter.

Figure 11:
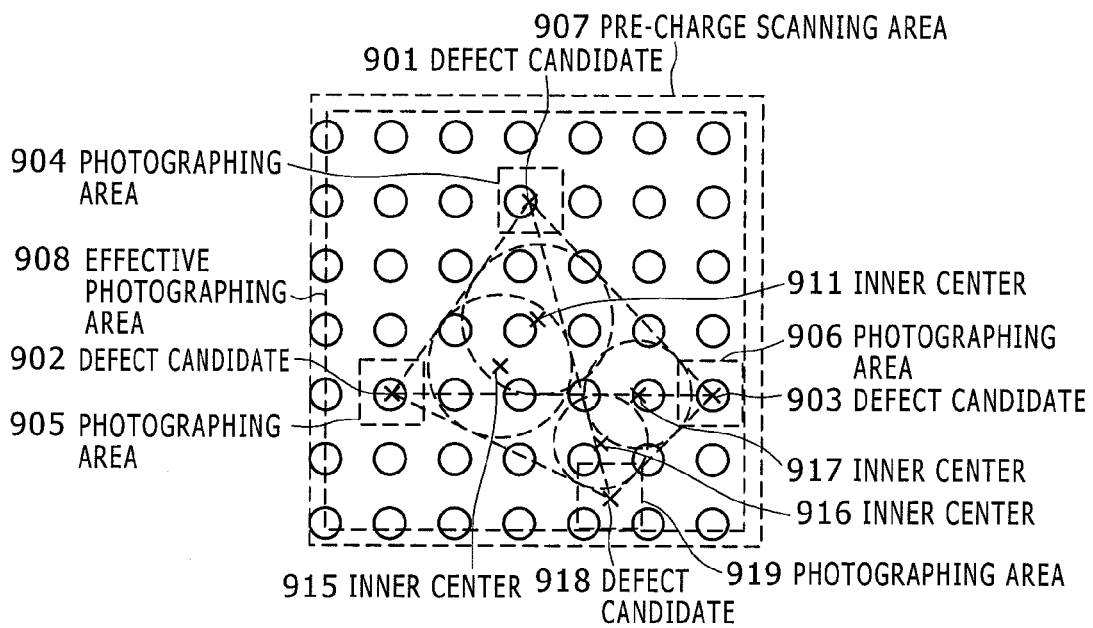
FIG. 11 is a diagram schematically showing the case where there are four defect candidates in a pre-charge scanning area.
Figure 12:
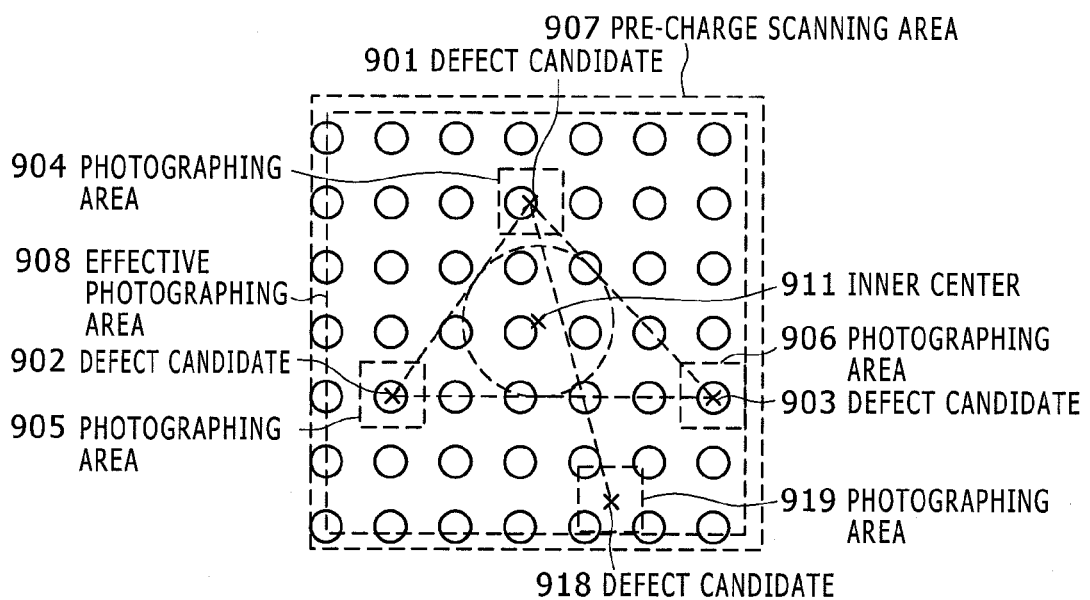
FIG. 12 is a diagram showing the case where the photographing area of one of four defect candidates located in a pre-charge scanning area adjoins the pre-charge scanning area.

For example, FIG. 12 shows the case where it is assumed that, taking the coordinate positions of the defect candidates shown in FIG. 11 into consideration, an optimal inner center is the inner center 911 of a triangle that has the defect candidates 901, 902, and 903 as its vertexes. In this case, the borders of photographing areas 906 and 919 are located very near to an effective photographing area 908, and it can be said that photographing areas 904 and 905 are far apart from the border of the effective photographing area 908 compared with the photographing areas 906 and 919. Here, if the center of the view field is corrected and the photographing areas of the defect candidates are uniformly apart from the effective photographing area 908, the coordinate positions of the defect candidates 901 and 902 get away from the center of the view field of the pre-charge scanning area 907, therefore it can be said that photographing conditions for the defect candidates 901 and 902 get worse in this case. This is an inevitable problem because the charge potential is gradually lowered as the observation point of the charge potential is apart from the center of the view field of the pre-charge scanning area. Therefore, it is desirable to make it switchable whether the coordinate position of the obtained inner center is kept the center of the view field as it is, or the coordinate position of the obtained inner center is corrected to be used as the center of the view field in accordance with the material of a specimen, inspection conditions, or the like just like the electron optical system conditions. In addition, if the distances between the photographing areas of the defect candidates and the effective photographing area are managed as attached information of photographed images, when any abnormalities of the photographed images are found here and there, it can be judged whether these abnormalities are induced by the decreases of charge potentials that occur owing to the coordinate positions getting apart from the center of the view field of the pre-charge scanning area or not. In addition, this attached information can be utilized for deriving electron optical system conditions required for executing optimal pre-charging well-adapted to the material of a specimen, the surface shape of a specimen, and the like.

In addition, although one method in which the center of the view field of a pre-charge scanning area for grouped defect candidates is obtained from the inner centers of triangles having the coordinate positions of the defect candidates as their vertexes has been described, the center of the view field can be obtained from the gravity center or the circumventer of the coordinate positions of the defect candidates as an alternative method without problems. If the gravity center of the coordinate positions of defect candidates is used, it is not necessary to calculate the inner centers of all triangles differently from the above. If the circumcenter is used, because three defects that constitute the triangle are equally distant from the center of the view field, the defect candidates in the group can be photographed under the same charge condition even when one-step pre-charging is executed.

Figure 13:
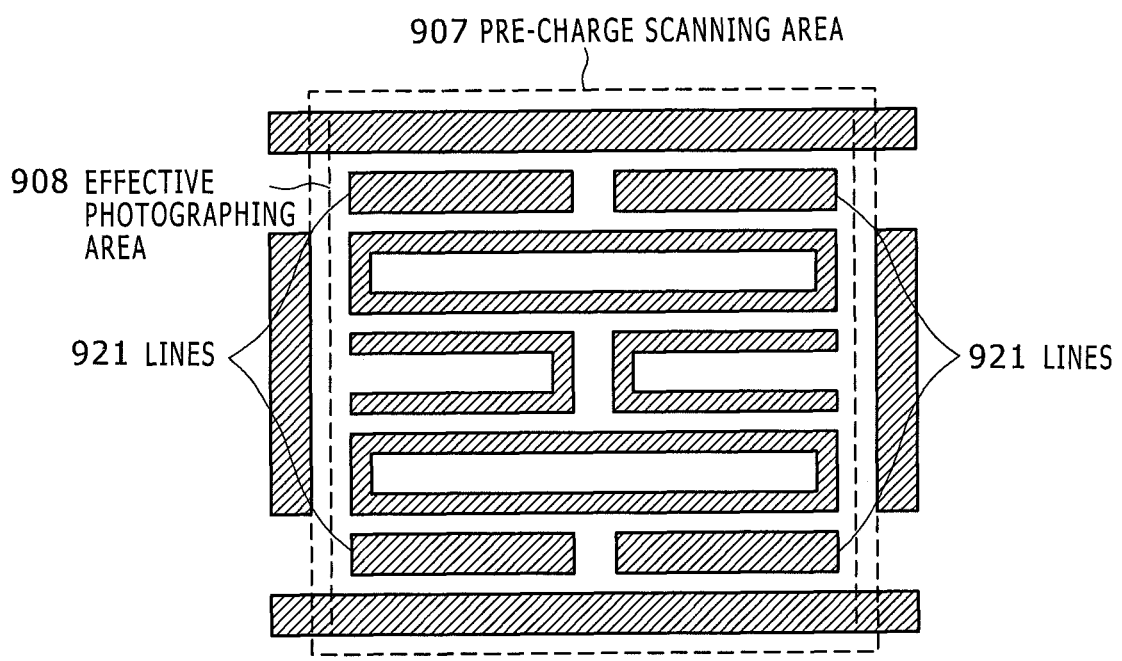
FIG. 13 is a diagram schematically showing lines and space patterns formed on a specimen.

Because the above-described grouping technique relevant to a pre-charge scanning area is a technology for reducing the risk of dielectric breakdown with the use of charge control when observation targets are closely located, this technology can be applied not only to contact holes whose patterns are formed on the surface of a specimen by miniaturization and integration in semiconductor manufacturing processes. For example, because observation targets are often located very closely in the measurement and observation of the dimensions of lines and space patterns of a deep groove structure as shown in FIG. 13, this technology can be effectively applied to these observation targets. In addition, it goes without saying that this technology can be applied to the measurement of line widths or the observation of the finish of patterns in the above case. Therefore, observation targets are not restricted to defect candidates, so line widths and specified patterns that are set in advance for observation are also referred to as observation targets hereinafter. In addition, the position of an observation target is referred to as an observation target portion hereinafter. Because measuring points are densely located, and there are plural lines 921, which are to be measured, within the effective photographing area 908 of a pre-charge scanning area 907 in FIG. 13, this technology can be used to reduce the risk of dielectric breakdown.

Second Embodiment

Next, a second embodiment, in which photographing of a low magnification image and photographing of a high magnification image are executed after common pre-charging although the pre-charging is executed for each defect candidate, will be described. In the case where defect candidates are not located near to each other, or in the case where the duration of charging effect is not long enough for the inspection sequence of photographing plural defect candidates, the plural defect candidates cannot be observed in the common pre-charge processing. In such a case, although the plural defect candidates cannot be dealt at the same time by a piece of pre-charge processing after grouping the plural defect candidates, if the duration (n seconds) of the charging effect for a photographing area is larger than time (m seconds) required by an inspection sequence for one defect candidate (including time required for photographing a low magnification image, time required for switching optical conditions, and time required for photographing a high magnification image) (that is, if n>m) as described above, both photographing of the low magnification image and photographing of the high magnification. image can be executed after the common pre-charging.

The flowchart from magnification being switched to low magnification to photographing a high magnification defect image in this embodiment is shown in FIG. 14. Compared with the inspection flow shown in FIG. 3(b) in which conventional pre-charge processing is executed, the flow from step 301 to step 307 according to this embodiment is the same. On the other hand, according to this embodiment, step 310 involving pre-charge processing between step 308 and step 309 can be omitted.

In other words, in conventional pre-charging, three pieces of pre-charge processing are needed for a defect candidate before low magnification reference image photographing, low magnification defect image photographing, and high magnification defect image photographing, while only two pieces of pre-charge processing are needed for a defect candidate before low magnification reference image photographing, and low magnification defect image photographing in this embodiment. Therefore, because only a piece of charge processing is executed for one portion, the risk of dielectric breakdown can be reduced. In addition, because time required by a piece of pre-charging can be omitted for one defect candidate, the throughput is improved.

Whether low magnification default image photographing and high magnification default image photographing can be executed after the common pre-charging, that is, whether the condition n>m is satisfied or not, can be automatically judged depending on an observation target with the use of plural flows stored in advance in accordance with various materials of specimens, conditions of defect candidates of observation targets, or electron optical system conditions. Alternatively, when inspection conditions are set, the above mentioned various conditions can be set by an operator via the manipulation unit 132.

The above described steps are executed by the operation unit 137 included in the total control unit 136.

In addition, the second embodiment can be applied not only to the case where there are not defect candidates closely located, but also can be applied to the case where the above described grouping is not executed, and low magnification photographing and high magnification photographing are executed on all defect candidates all together after one common pre-charging.

The above described structure of the second embodiment makes it possible to reduce the risk of dielectric breakdown owing to the overlapping of pre-charge scanning areas. In addition, because it is not necessary to install hardware dedicated to execute electricity removal on the overlapping area of pre-charge scanning areas, there is no need to modify an existing device structure, therefore price competitiveness in the marketplace is not impaired. Because it is possible to perform a successive inspection sequence in which pre-charging can be executed under optimal electron optical system conditions, the defect detection sensitivity of this embodiment becomes higher than the defect detection sensitivity of a method in which pre-charging is executed with charge efficiency lowered. In addition, because the number of pre-charging executions can be reduced, the throughput of the inspection sequence can be improved.

LIST OF REFERENCE SIGNS

101 Electron Optical System
102 Charged Particle Source
103 Specimen
104 Specimen Exchange Room
105 Specimen Room
106 Specimen Stage
107 Amplifier
108 High Voltage Control Unit
109 Retarding Voltage Control Unit
110 First Condenser Lens Control Unit
111 Second Condenser Lens Control Unit
112 Alignment Control Unit
113 Deflecting Current Control Unit
114 Object Lens Control Unit
115 Pullout Electrode
116 Primary Electron Beam
117 First Condenser Lens
118 Second Condenser Lens
119 Alignment Coil
120 Object Lens
121 Secondary Electron Beam
122 Detector
123 Defect Detection Control Unit
124 Automatic Defect Classification Control Unit
125 Display Monitor
126 Image Memory
127 Image Processing Control Unit
128 Image Correction Control Unit
129 Image Display Unit
Electron Optical System Control Unit
131 Device Control Unit
132 Manipulation Unit
133 I/O Interface
134 Stage Control Unit
135 Delivery Control Unit
136 Total Control Unit
137 Operation Unit
201 Semiconductor Wafer
202, 501, 502, 503, 701, 702, 703, 704, 801, 802, 901, 902, 903, 918 Defect Candidate
401, 507, 508, 509, 803, 907 Pre-charge Scanning Area
402 Photographing Area at a Low Magnification 1,000
403 Photographing Area at a Low Magnification 10,000
404 Contact Hole
405 Additional Area
504, 505, 506, 904, 905, 906, 919 Photographing Area
510 Overlapping Area
804 Intermediate Coordinates
908 Effective Photographing Area
909 Triangle
910 Inscribed Circle
911, 915, 916, 917 Inner Center
920 Distance α
921 Line

The invention claimed is:

1. A charged particle beam apparatus comprising:
a specimen stage configured to transfer a specimen;
a charged particle optical system configured to irradiate a charged particle beam generated from a charged particle beam source to the specimen;
a control unit configured to control the charged particle optical system and the specimen stage;
a detector configured to detect secondary particles generated from the specimen by the irradiation of the charged particle beam;
an image processing unit configured to generate an image of the specimen from the secondary particles;
a scanning area setting unit configured to set a scanning area of the charged particle beam, in a charge control process to control the charge condition on the specimen;
an operation unit configured to group a plurality of observation target portions included in the scanning area into groups, based on a magnification on which the charge control process is to be executed, or a size of the scanning area scanned by the charged particle beam used in the charge control process, wherein all observation target positions included in one of the groups are processed together in one charge control process; and
wherein the image processing unit is configured to generate a plurality of images on the basis of a piece of charge control processing executed on the scanning area.

2. The charged particle beam apparatus according to claim 1,
wherein the operation unit is configured to judge whether or not an observation target portion is included in an area where charge control can be executed on observation target portions all together, in view of the position of the observation target and a magnification used for the charge control, or the size of an area scanned with the charged particle beam used when the charge control is executed.

3. The charged particle beam apparatus according to claim 1,
wherein the operation unit is configured to judge whether or not an observation target portion is included in an area where charge control can be executed on observation target portions all together, in view of a quantity of time required for photographing one observation target portion and a duration of a charging effect.

4. The charged particle beam apparatus according to claim 3,
wherein the operation unit further is configured to judge on the basis of a magnification or the size of a view field used when the observation target portion is observed after the charge control is executed.

5. The charged particle beam apparatus according to claim 1,
wherein the scanning area setting unit is configured to set a scanning area, so that the photographing areas of all observation target portions are located inside the scanning area with a predetermined distance apart from the border of the scanning area.

6. The charged particle beam apparatus according to claim 5, further comprising:
an input unit configured to enable the user to change the distance.

7. The charged particle beam apparatus according to claim 1,
wherein the scanning area setting unit makes the gravity center of the positions of observation target portions included in the group, or the inner center or the circumcenter of any three points of the positions of observation target portions the center of the scanning area.

8. The charged particle beam apparatus according to claim 1, further comprising
a route calculation unit that calculates a route that makes a stage transfer distance the minimum, wherein
the operation unit groups the plurality of observation target portions into the groups after the route is calculated.

9. The charged particle beam apparatus according to claim 1,
wherein algorithms are switched in accordance with the number of executions of charge control made on the scanning area.

10. The charged particle beam apparatus according to claim 1,
wherein the position coordinates of the observation target portions are input from an external inspection device.

11. A charged particle beam apparatus configured to observe a specimen on which a plurality of observation target portions are located, wherein the charged particle beam apparatus:
sets a scanning area of a charged particle beam in a charge control process to control the charge condition on the specimen;
groups a plurality of observation target portions included in the scanning area into groups based on a magnification on which the charge control process is to be executed or a size of the scanning area scanned by the charged particle beam used in the charge control process;
executes pre-charging on the scanning area, wherein all observation target positions included in one of the groups are processed together in one charge control process; and
observes observation target portions included in the group in a photographing area smaller than the scanning area.

12. A defect observation method comprising the steps of:
inputting the position coordinates of a plurality of observation target portions and optical conditions, including a scanning area of the charged particle beam in a charge control process to control the charge condition on the specimen;
grouping the plurality of observation target portions included in the scanning area into groups based on a magnification on which the charge control process is to be executed or a size of the scanning area scanned by the charged particle beam used in the charge control process;
executing the charge control process on a specimen by scanning the area with a charged particle beam, wherein all observation target positions included in one of the groups are processed together in one charge control process; and
observing the observation target portions on which charge control is executed.

13. The defect observation method according to claim 12, comprising the step of:
determining observation target portions, on which charge control is executed all together, on the basis of time required for photographing one observation target portion and the duration of the charging effect in addition to the magnification used when the charge control is executed or the size of an area scanned with a charged particle beam used when charge control is executed.

14. The defect observation method according to claim 12, further comprising the step of:
setting an area where scanning accompanied with charge control is executed so that the photographing areas of the observation targets are not included within a predetermined distance from the border of the area where the scanning accompanied with the charge control is executed.

* * * * *